(12) United States Patent
Barkhahn et al.

(10) Patent No.: US 7,435,240 B2
(45) Date of Patent: Oct. 14, 2008

(54) FLEXIBLE INJECTION NEEDLE

(75) Inventors: Susanne Barkhahn, Bern (CH); Andreas Reinmann, Luterbach (CH)

(73) Assignee: Disetronic Licensing AG, Burgdorf (CH)

( * ) Notice: Subject to any disclaimer, the term of this patent is extended or adjusted under 35 U.S.C. 154(b) by 256 days.

(21) Appl. No.: 11/182,524

(22) Filed: Jul. 15, 2005

(65) Prior Publication Data

US 2005/0283125 A1    Dec. 22, 2005

Related U.S. Application Data

(63) Continuation of application No. PCT/EP2004/000309, filed on Jan. 16, 2004.

(30) Foreign Application Priority Data

| Jan. 17, 2003 | (CH) | ..................................... 0073/03 |
| Feb. 13, 2003 | (DE) | ................................ 103 06 013 |

(51) Int. Cl.
*A61M 5/32* (2006.01)
(52) U.S. Cl. .................. 604/272; 604/525; 604/530
(58) Field of Classification Search ................. 604/272, 604/525, 530
See application file for complete search history.

(56) References Cited

U.S. PATENT DOCUMENTS 2,828,744 A    4/1958   Hirsch et al.
4,950,258 A  * 8/1990   Kawai et al. ................. 604/530
4,976,704 A   12/1990   McLees
5,441,489 A  * 8/1995   Utsumi et al. ................ 604/525
5,624,727 A    4/1997   Stoy
5,762,630 A  * 6/1998   Bley et al. ............. 604/164.01
5,853,408 A  * 12/1998  Muni ........................... 606/27
5,885,258 A  * 3/1999   Sachdeva et al. ............ 604/530
6,096,023 A  * 8/2000   Lemelson .................... 604/524
6,126,633 A   10/2000   Kaji et al.

FOREIGN PATENT DOCUMENTS

| DE | 197 38 942 A1 | 3/1999 |
| EP | 0 529 675 B1  | 2/1996 |
| WO | WO 02/28458 A1 | 4/2002 |

* cited by examiner

*Primary Examiner*—Nicholas D. Lucchesi
*Assistant Examiner*—Aarti Bhatia
(74) *Attorney, Agent, or Firm*—Dorsey & Whitney LLP

(57) ABSTRACT

An injection needle, for injection into a body tissue, is flexible in the introduced or post-inserted state and comprises a channel for the introduction of a fluid. The injection needle is at least partly made from at least one material which is rigid in one state and flexible in a second state. Alternatively or concurrently, the injection needle is rigid on application of a force to the needle along the longitudinal direction of a needle longitudinal axis and is flexible on application of a force in the radial direction relative to the needle longitudinal axis.

21 Claims, 7 Drawing Sheets

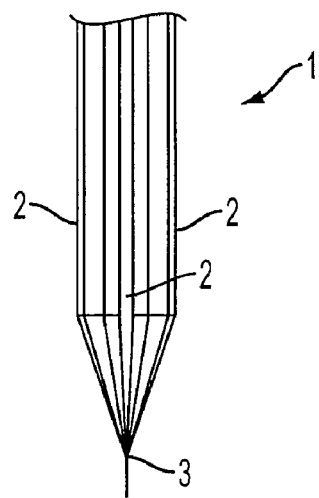
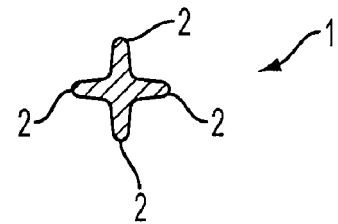
FIG. 1b
FIG. 1a
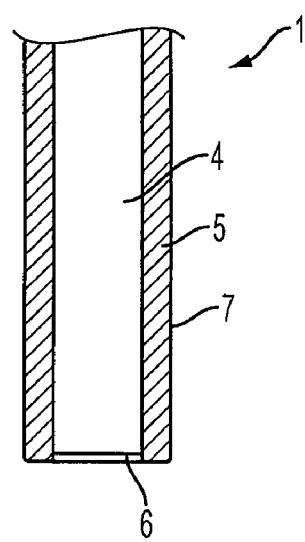
FIG. 1c
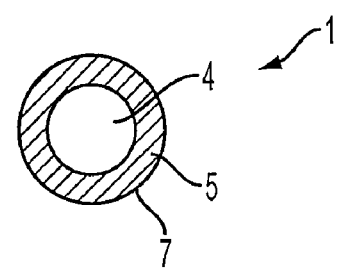
FIG. 1d

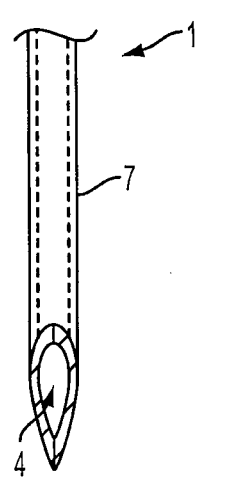
FIG. 7a
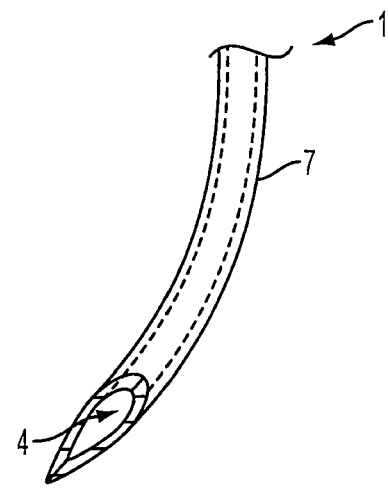
FIG. 7b
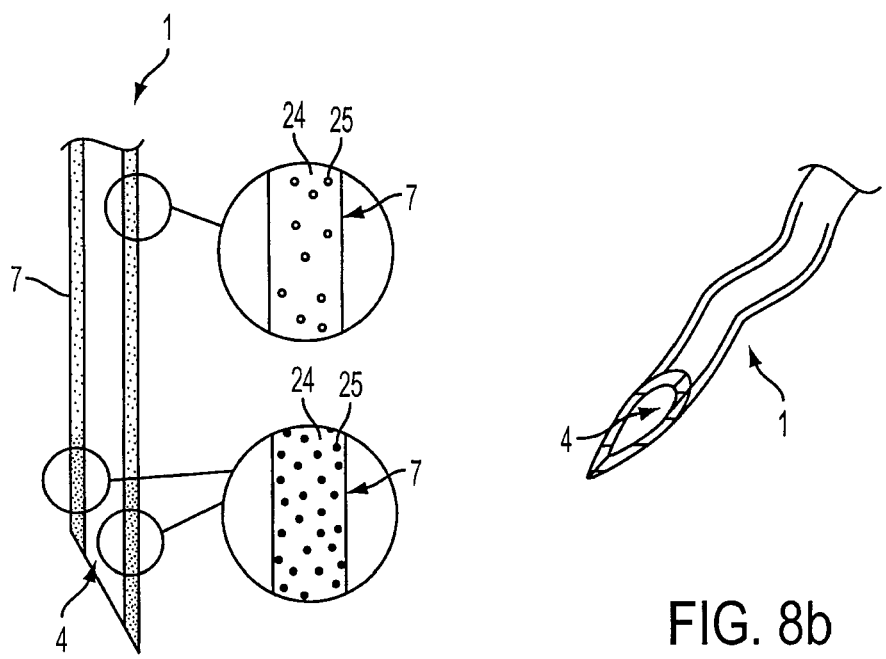
FIG. 8a
FIG. 8b

FLEXIBLE INJECTION NEEDLE

CROSS-REFERENCE TO RELATED APPLICATION(S)

This application is a Continuation of International Application No. PCT/EP2004/000309, filed on Jan. 16, 2004, which also claims priority to Swiss application No. 0073/03, filed on Jan. 17, 2003, and German Application No. 103 06 013, filed on Feb. 13, 2003, the content of both applications are incorporated in their entirety herein by reference.

BACKGROUND

The invention relates to delivery, administration or injection of a substance through a needle, conduit ir the like. More particularly, it relates to an injection needle for injection into body tissue, preferably into or through the human skin, which injection needle is flexible in the inserted state and conveys a fluid to be administered into the tissue. The injection needle preferably forms an inner channel through which the fluid is conveyed, i.e. it preferably forms an injection cannula.

In a great many therapeutic or diagnostic applications it is necessary for an injection needle to be placed in or lodged in body tissue over quite a long period of time, for example in order to permit repeated or sustained administration of therapeutic or diagnostic fluids. In the treatment of patients with diabetes, for example, insulin is administered at regular intervals through an injection needle which remains in the patient's body tissue over a period of several days.

For this purpose, it is known from U.S. Pat. No. 4,562,751, for example, to use an injection needle made of steel. A steel needle does have a simple structure, but it also has various disadvantages. The sharp needle tip of the rigid injection needle can cause constant irritation of the surrounding tissue since it cannot adapt to the movements of the tissue. Such a rigid injection needle, when inserted, is uncomfortable for the patient and even painful. There is also a considerable risk of needlestick injuries to the tissue surrounding the needle tip and also when removing the injection needle from the tissue.

Devices referred to as soft cannulas and which are flexible have therefore been developed. U.S. Pat. No. 4,755,173, for example, describes an injection set used for subcutaneous administration of a fluid, in which a steel needle is guided through a soft cannula so that the sharp tip of the steel needle protrudes from the soft cannula. With the aid of the steel needle, the soft cannula is inserted into body tissue. The steel needle is then removed from the soft cannula, as a result of which a fluid connection is established between the soft cannula and the tissue.

A soft cannula of this kind can easily follow the movements of the tissue, so that there is no irritation, or only slight irritation, of the surrounding tissue. To insert the soft cannula, however, it is still necessary to use a rigid injection needle, for example a steel needle, which has to be removed after the soft cannula described has been inserted. The soft cannula therefore also poses the risk of a needlestick injury. In addition, the opening through which the steel needle has been removed has to be sealed off to permit correct use of the injection needle. This procedure is complicated and increases the risk of a lack of leaktightness when fitting the cannula.

SUMMARY

Objects of the present invention are to simplify the handling and structure of an injection needle for injection into body tissue, to reduce the number of individual parts needed for injection, to make the injection needle comfortable to wear, and to further reduce the risk of needlestick injuries when handling the injection needle.

These objects are addressed by providing an injection needle for injection into body tissue, which injection needle is flexible after being inserted and has a channel for introduction of a fluid, wherein the injection needle is made at least partly from at least one material which, in a first state, has a flexural strength sufficient for the injection and, in a second state, has a reduced flexural strength. In some embodiments, the injection needle has a longitudinal axis and is rigid when a force acts on the injection needle in the longitudinal direction and is flexible when a force acts in the radial direction relative to the longitudinal axis.

Accordingly, the invention provides an injection needle for injection into body tissue, which injection needle is flexible in the inserted state and preferably has an inner channel, or bore or lumen, for introduction of a fluid. Before insertion into the body tissue, the injection needle has a sufficient rigidity to be able to penetrate the surface of the body tissue and to be able to be inserted farther into the tissue. According to the invention, the injection needle is made at least partly from a material which, in a first state, is flexurally rigid and, if appropriate, also resistant to other stresses, and, in a second state, is flexible, preferably elastic. The first state is characterized in that the injection needle has a sufficient rigidity and, at least at a tip, a sufficient hardness to be able to be pushed into the body tissue. The second state is characterized in that the material used is, for example, bendable in different directions radially with respect to a longitudinal axis of the injection needle or is compressible and then expandable again, but forms a sufficient inner channel and/or optionally outer channel for conveying the fluid into the tissue.

In some embodiments, the present invention comprises a device, e.g., a needle, catheter, cannula, or a portion thereof, for penetrating body tissue, said device comprising a lumen for introduction of a fluid to the body tissue and at least one material which, in a first state, has a flexural strength sufficient for penetrating the body tissue and, in a second state, has a reduced flexural strength. In some embodiments, the device has a longitudinal axis and is substantially rigid when a force acts on the device in a longitudinal direction and is generally flexible when a force acts in the radial direction relative to the longitudinal axis.

In preferred embodiments, the bendable injection needle is made along its entire length, or at least partly, from a material which, in the first state of the injection needle, has an elastic modulus of over 1000 MPa, preferably 2000 MPa or more. The material ought even to have an elastic modulus of at least 3000 MPa. During insertion, or preferably a certain time after insertion, which should be not longer than 20-30 minutes, the elastic modulus of the material changes and should then be not more than 1000 MPa. In the second state, its elastic modulus is preferably less than 800 MPa. A particularly preferred material has, in the first state, an elastic modulus of 3000 MPa or above and, in the second state, an elastic modulus of 700 MPa±100 MPa.

The material of modifiable elastic modulus can be a homogenous material or a composite material. In preferred embodiments, it is possible to use a shape-memory material, preferably a polymer or a gel, for example a polymer gel, or a combination of several shape-memory materials.

The material of modifiable elastic modulus can, as composite material, in particular be composed of a support matrix material, preferably a plastic material, and of a filler embedded in the support matrix. The filler should be formed from a hard and rigid material which has an elastic modulus of preferably at least 5000 MPa and is preferably present in small particles. Suitable filler materials are ceramic materials in particular, but also glass, metal, or even polymer substances. The filler should have a volume proportion of at least 5% and at most 95%, preferably at most 80%, of the composite material. Instead of compact particles, the filler can also be a fiber material whose fibers are preferably substantially shorter than the injection needle. The filler material can be distributed in the support matrix uniformly along the length of the injection needle, so that the stiffening obtained by means of the filler material in the first state of the injection needle is uniform along the entire length of the latter. Alternatively, however, the filler material can also be distributed differently in some areas in order to influence the rigidity of the injection needle in targeted ways. Thus, the concentration of the filler material can be greater at the tip of the injection needle in particular than in the shaft area. In such a configuration, the concentration, i.e. the volume proportion, of the filler material at the tip is between 50 and 80% and is less than 50% in the shaft area, preferably between 5 and 20%, or still more preferably between 10 and 20%. The transition between a section with a high proportion of filler material and a section with by comparison a lower proportion of filler material is preferably continuous, but it can also be made abrupt, i.e. non-continuous. A variation in the proportion of filler material, for example decreasing from the tip of the injection needle to its proximal end, can be achieved, for example, by extrusion of the injection needle, the filler material being fed to the extruder in a volume flow corresponding to the volume proportion in the injection needle, and the support matrix being admixed with the material in the extruder. The support matrix material is preferably a shape-memory material whose elastic modulus decreases in the inserted state, or even during insertion itself. The material of the support matrix can, with respect to the elastic modulus, have the properties described above. By means of the embedding of the filler material, however, the elastic modulus of the support matrix material outside the tissue, i.e. before insertion, can also be lower than in the case of a material of modifiable elastic modulus without any introduced filler material.

Materials of modifiable elastic modulus that can be used are, in particular, plastic materials, preferably thermoplastic polymers. The change in the material property according to the invention, preferably expressed by the change in the elastic modulus of the material in question, is advantageously based on the transition to the amorphous state. The transition can in particular be based on the change in temperature or pH or on a chemical reaction of the material with a surrounding medium, or on a combination of several of these factors. A preferred material is a thermoplastic polymer with a glass transition temperature of at least 30° C., preferably at least 32° C., and of at most body temperature, i.e. at most ca. 37° C., preferably at most 36° C. Instead of using a material with a glass transition temperature in the desired range, or in combination with such a material, it is possible to use a material with a melting temperature lying at or below body temperature but above the ambient temperature. Accordingly, it is possible to speak in quite general terms of a switching temperature, which in particular can be the glass transition temperature or the melting temperature, or in principle also a temperature at which another transition of the material takes place, provided that the flexibility changes when the needle has warmed at least to the switching temperature. The switching temperature should be at least 30° C. to ensure that the needle assumes the first state under the customary ambient temperatures.

Although plastics are preferred needle materials, the injection needle can in principle also be made from another material which is biocompatible and undergoes the change of state.

Instead of bringing about a change in the flexural strength of the injection needle by changing the elastic modulus, the flexural strength can also be changed by modifying the critical moment of inertia of the injection needle, i.e. by changing the shape of the injection needle or at least a section of the injection needle. Finally, the flexural strength can also be changed by a combination of varying the elastic modulus and also the moment of inertia.

It is preferable if the tip of the injection needle is soft in the second state, i.e. is made from the material of modifiable elastic modulus. In principle, however, it is also possible for the tip to be made permanently rigid. However, it should then be as short as possible, at least so short that, in the inserted state, a flexible section of the injection needle adjoins the tip, which in this case is also rigid in the inserted state, in order to alleviate pain by permitting a yielding movement, preferably bending, of the injection needle in the inserted state.

In one embodiment, the injection needle according to the invention is made completely from a shape-memory material. The shape-memory material is preferably of tubular configuration for the formation of the injection needle, so that an inner space can be formed as an inner channel for passage of the fluid. In the first state, the tube made from shape-memory material has a form in which at least one pointed edge is formed on the circumference of the tube or injection needle, that is to say the edge has an acute angle so that it can serve as, a kind of cutting edge for insertion of the injection needle. In this first state, there does not have to be a hollow space formed in the inside of the tube made from shape-memory material. In fact it is preferable for no hollow space or channel to be formed in the first state. The inner surfaces of the wall of the tube bear on one another. Moreover, in this first state, a solid and preferably closed tip is formed at an end of the injection needle serving for insertion into the body tissue. The tip of the injection needle then has no opening, and instead it consists of a solid area of shape-memory material. In principle, however, the tip can also be open.

In one preferred configuration as injection cannula, the injection needle preferably acts like a tube in the second state, while its properties in respect of the injection itself correspond to those of a pipe, in other words the injection needle in the preferred configuration as injection cannula is like a pipe in the first state. The modifiable material, however, can also be tubular in the first state if it is stiffened to acquire the necessary rigidity for insertion. When the terms "tube" and "tubular" are used below, they are intended to describe the injection needle in a preferred configuration as injection cannula in the second state, in which case such an injection needle can be, but does not have to be, pipe-like in the first state.

In the rigid, first state, the injection needle can be easily pushed into the tissue surface by means of its tip, without any other aid, and, by means of a cutting edge extending in the longitudinal direction of the injection needle, can be inserted farther into the tissue. In the first state, the tube made from shape-memory material is preferably folded in the longitudinal direction of the injection needle in such a way that the inner surfaces of the wall of the tube come to bear on one another and four folds arranged in a cross shape, preferably at right angles, form along the longitudinal axis of the injection needle. In principle, however, the tube could also be folded in such a way that three folds or even five folds or more form along the longitudinal axis of the injection needle. If the inner surfaces of the tube are folded onto one another, the injection needle has no inner hollow space in the first state.

After insertion of the injection needle, the shape-memory material changes from the first form, which constitutes the first state, to a second form, which constitutes the second state of the injection needle. In this second form, the circumference of the tube or of the injection needle preferably has an edgeless configuration, and an inner channel is formed extending along the longitudinal axis of the injection needle, and an opening is formed in the direction of the longitudinal axis of the injection needle at the end, i.e. at the tip of the injection needle. To do this, the tube made from shape-memory material unfolds, for example, so that the edges formed by the folds are smoothed out. This unfolding results in the inner channel which extends along the longitudinal axis of the injection needle and which emerges as an opening from the end of the injection needle in the direction of the longitudinal axis. In this second, unfolded state of the injection needle inserted into the body tissue, a fluid can be introduced into the tissue by way of the inner channel and the opening.

In another embodiment of an injection needle according to the invention, it comprises an elastic tube, preferably made from shape-memory polymer, which is preferably also expandable. In the inner space formed by the tube, rigid fibers, preferably carbon fibers or glass fibers, are arranged along the longitudinal axis of the injection needle. In a first form, i.e. the first state of the injection needle, the injection needle is solid, since the fibers are pressed together by the tube, and it preferably has no hollow spaces in the inside. In this compact form, the injection needle is sufficiently rigid, because the fibers stiffen each other, to be able to be inserted into the tissue. The tube can be shrunk onto the fibers and enclose them. In a second form, that is to say the second state of the injection needle, the tube has expanded. The fibers lie loosely in the tube and only the flexural strength of the individual fibers still counteracts bending.

In yet another embodiment, the injection needle according to the invention comprises a tube which, in some parts of its wall, has areas made from shape-memory material. The sections of the wall lying between the areas of shape-memory material are advantageously rigid. The areas of shape-memory material are preferably configured as folded areas whose folds extend perpendicularly with respect to the longitudinal axis of the injection needle, that is to say the tube is shortened by the folds. In a first form of the shape-memory material, the folds come to bear on one another. The folds, that is to say the areas of shape-memory material, cannot thus be further compressed in the direction of the longitudinal axis of the injection needle and the injection needle is so rigid that it can be pushed into the tissue. In a second form, the shape-memory material assumes an expanded shape with the folds drawn apart from one another. In this form, the areas of shape-memory material along the longitudinal axis of the injection needle are compressible and expandable. The injection needle is thus movable in a radial direction with respect to the longitudinal axis of the injection needle. The areas of shape-memory material are preferably arranged as annular areas around the circumference of the injection needle tube. At these annular areas, the injection needle in the second form, that is to say in the second state, is then able to follow the movements of the tissue after insertion into the latter.

In a further embodiment, the front area of the tube is provided with an insertion aid which, in the first state of the injection needle, protrudes longitudinally past the end forming the tip of the injection needle. The insertion aid can be formed, for example, by a needle tip which, with the aid of an extension, is secured on the injection needle at an attachment point provided at a distance from the injection needle tip. This means the attachment location of the insertion aid does not lie at the distal end of the injection needle, but instead at a proximal location remote from the latter. In the first state, in which the folds of the shape-memory areas come to bear on one another, the tip protrudes from the end of the injection needle tube. Several areas of shape-memory material, as described above, are provided between the tip of the insertion aid and its attachment point. In the second state of the injection needle, these areas are unfolded so that the injection needle section between the attachment point and the injection needle end lengthens. By this means, the injection needle tube is pushed out over the insertion aid, so that it can serve as protection for the insertion tip.

Instead of having a folded configuration, the areas of shape-memory material in the wall of the injection needle tube can of course also have another form, as long as they have sufficient rigidity in a first state of the injection needle and have sufficient flexibility, preferably pliability, in a second state of the injection needle. For example, the areas can also have a perforated configuration. As perforations, for example, the wall of the tube can be provided with small slits which, for example, extend in succession in the circumferential direction and are arranged in several rows alongside one another. The slits can be formed only in a surface of the tube or they can also be formed right through the wall. In a first form of the areas of shape-memory material, the slits come to lie on one another. In a second form, the slits are widened out to provide pliability in a radial direction with respect to the longitudinal axis of the injection needle.

In another embodiment, the injection needle is made, at least in some areas, from at least one gel. The injection needle is preferably formed from a tube which, in at least some parts of its wall, has one or more hollow spaces extending in the longitudinal direction of the longitudinal axis of the injection needle. The tube therefore comprises at least an inner channel, for passage of a fluid, and hollow spaces provided inside the wall. The hollow spaces inside the wall are filled with gel. The tube itself is made of elastic, flexible material. It is also possible to provide the gel in a tubular sheath and to arrange the sheath on an outer surface or inner surface of the injection needle tube.

In a first state, the gel is solid. In this state, it forms a support structure for the injection needle tube which is thus made sufficiently rigid to be inserted into body tissue. In a second state, the gel is soft, so that the hollow spaces filled with gel, or the gel sheath, are elastic and do not provide a support action for the injection needle tube.

The change between a first, rigid state and a flexible, preferably elastic, second state of the material of the injection needle permits simple handling when inserting the injection needle into tissue, without the need for several different individual parts. The change of state between the first state and the second state of the material of the injection needle can be obtained through a means of changing state which, for example, applies a voltage or radiation to the injection needle, or to the material according to the invention of the injection needle. The change of state can also be obtained by the effect of a chemical reaction, a change of temperature or a change of pH. This can be achieved, for example, through the change of environment of the injection needle upon insertion into the tissue, that is to say the surrounding medium of the tissue, or by a fluid passed along the injection needle. The change of state is preferably reversible. This means that the injection needle can be brought from a rigid, first state to an elastic, second state, and then back to a rigid, first state.

According to a further aspect of the present invention, the injection needle is rigid when a force acts on the injection needle in the longitudinal direction of a longitudinal axis of the injection needle, and elastic when a force acts in a radial direction with respect to the longitudinal axis of the injection needle. To insert the injection needle, the latter is placed with the injection needle tip on the surface of the body tissue and is pressed onto the latter. In doing this, a force acts in the longitudinal direction of the axis of the injection needle. Under the action of such a force, the injection needle is rigid and does not yield. Inside the body tissue, forces acting laterally on the injection needle arise, for example, through movements of the patient's muscles, that is to say forces acting in a radial direction with respect to the longitudinal axis of the injection needle. The injection needle behaves elastically with respect to this force, that is to say it yields in this direction.

In one embodiment, the injection needle comprises a tube whose wall has rigid areas alternating with flexible areas which permit bending of the tube radially with respect to the longitudinal axis of the injection needle. The flexible areas can, for example, be obtained by a folding of the wall or by a perforation of the wall. These areas can be configured in the same way as has been described above for areas of shape-memory material. However, the areas do not have to be made from shape-memory material. The rigidity or flexibility of the injection needle is obtained, in this embodiment, from the particular structure of the tube wall. In the case of a folding of the wall, the folded areas cannot be further compressed when the individual folds come to bear on one another. Under the action of a suitable force for compression, that is to say a force acting in the longitudinal direction of the injection needle axis, these areas are therefore rigid. However, the folds can be drawn apart. If a fold area arranged annularly around the circumference of the tube is drawn apart more on one side than on the opposite side, this results in a bending of the tube or injection needle. The flexible and rigid areas of the tube wall alternate in such a way that the injection needle, in a state when inserted into the tissue, reacts to lateral forces by bending.

In another embodiment, the injection needle comprises an elastic tube whose interior receives a support structure. The support structure is movable in the radial direction with respect to the longitudinal axis of the injection needle and is rigid in a direction along the longitudinal axis of the injection needle. The support structure used can, for example, be a helical spring whose windings bear on one another when the helical spring is in the rectilinear state. The helical spring is introduced into the elastic tube in such a way that the tube comes to lie on the outer circumference of the spring. Between the windings, it is also possible to provide spacers by means of which the windings lie at a spacing on one another or on the spacers. By the contact of the windings, the helical spring is rigid when a force acts in the longitudinal direction of the spring or of the injection needle. In the event of a lateral force acting in a radial direction with respect to the longitudinal axis of the injection needle, the windings can lift from one another on one side and in this way permit bending of the helical spring or of the injection needle. Advantageously, the helical shape of the spring creates, at its end, an insertion tip for insertion of the injection needle into the tissue.

In yet another embodiment, an injection needle according to the invention comprises an elastic tube with an inner channel for passage of a fluid, that is to say an inner space extending along the longitudinal axis of the injection needle, and at least one clearance space formed in the wall of the tube. According to the invention, the clearance space is provided with a filler material which, in a first state, is compressed by a compression means in the direction of the longitudinal axis of the injection needle and, in a second state, is freed from its compression by release of the compression means. The filler material used can, for example, be a fiber material, granules, a gel or glass. By means of the compression of the filler material, the clearance space expands perpendicularly with respect to the longitudinal axis of the injection needle, as a result of which it becomes rigid and serves as a support for the injection needle. It preferably expands in the direction of the inner space of the tube, as a result of which the inner channel narrows, but the total circumference of the tube is not appreciably increased. When the clearance space is freed from its compression, the filler material spreads along the increased total length of the clearance space along the longitudinal axis of the injection needle and is substantially movable inside the clearance space, so that the injection needle becomes flexible. The compression means used can, for example, be a ring which is arranged around the tube and can be moved along the longitudinal axis of the injection needle. By the movement of the ring along the longitudinal axis of the injection needle, the filler material in the clearance space is compressed or freed from its compression.

In this embodiment, the outer wall of the elastic tube is preferably less stretchable and the inner wall, which serves as partition wall between the clearance space and the inner space, is made very stretchable. Upon compression of the filler material in the clearance space, the latter therefore expands mainly into the interior of the tube.

The present invention is set forth herein on the basis of illustrative embodiments. However, the individual features of individual illustrative embodiments can advantageously be combined with one another, for example in an embodiment of an injection needle with fold-like areas provided in the wall of the injection needle and made of shape-memory material. Other combinations of the features of the inventive injection needle are therefore also to be considered as belonging to the invention. Further, additional objects, features and advantages should be apparent from the descriptions herein and from the accompanying drawings.

BRIEF DESCRIPTION OF THE FIGURES

FIG. 1a is a schematic representation of an embodiment of an injection needle according to the present invention, in a rigid, first state, FIG. 1b is a cross section through the injection needle of FIG. 1a, FIG. 1c is a longitudinal section through the injection needle according to the first embodiment, in a flexible, second state, FIG. 1d is a cross section through the injection needle according to FIG. 1c, FIG. 7a shows an eighth embodiment of an injection needle according to the invention, in a rigid, first state, FIG. 7b shows the injection needle of the eighth embodiment in a flexible, second state, FIG. 8a shows a ninth embodiment of an injection needle according to the invention, in a rigid, first state, and FIG. 8b shows the injection needle of the ninth embodiment in a flexible, second state.

DETAILED DESCRIPTION

Figure 2A:
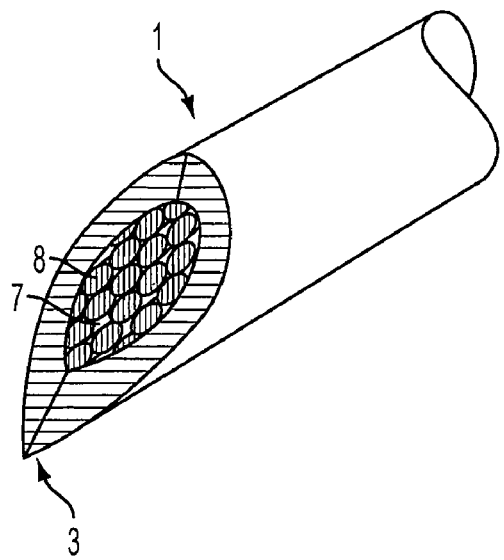
FIG. 2a is a schematic representation of a second embodiment of an injection needle according to the present invention, in a rigid, first state.

A first embodiment of an injection needle 1 according to the present invention is shown in FIGS. 1a through 1d. The injection needle is made substantially completely from a shape-memory material which is presented in a tubular form. In FIGS. 1a and 1b, the injection needle 1 is shown in a first form in which it assumes a rigid state suitable for insertion into a tissue. The shape-memory material in this state is formed like a folded tube so that four edges 2 are present. As can be seen from FIG. 1b, the four edges in this embodiment are arranged relative to one another in a cross shape. In the inside of the tubular shape-memory material, there is no hollow space in the first form. In a modification of this, however, a hollow space may be formed in the first state. One end of the tubular shape-memory material forms a tip 3 of the injection needle 1. At the tip 3, the edges 2 run together to a point. It is conceivable to provide an additional insertion aid at the tip 3, in the form of a hard and pointed element, in order to pierce the tissue surface. In this folded and rigid, first state, the folded edges 2 support one another. The injection needle is sufficiently rigid to be able to penetrate into body tissue.

In FIGS. 1c and 1d, the injection needle according to the first embodiment is shown in a flexible, second state in which the injection needle 1 has a reduced flexural strength compared to the first state, so that it is more flexible, preferably elastically flexible. By stimulation of the tubular shape-memory material, for example by heating or by incident radiation, the shape-memory material assumes its second form in which the injection needle is flexible and has an inner channel 4 for passage of a fluid. In this state, the injection needle assumes the form of a tube 7 in which the folding according to the first form is canceled and the tube 7 acquires a circular wall 5, as can be seen from the cross section in FIG. 1d. In this state, the injection needle has an open end as opening 6 through which a fluid can be delivered into the tissue. The flexibility in the second state is achieved through a reduced elastic modulus of the needle material. Alternatively, the cross-sectional shape and/or the size of the injection needle in the first state can be chosen such that, in the first state, it has a greater geometrical moment of inertia than in the second state. It is also conceivable that, in the first state, both the elastic modulus and also the moment of inertia are greater than in the second state.

Figure 2B:
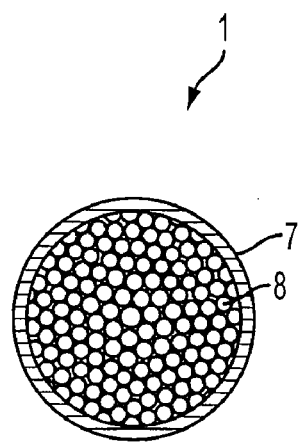
FIG. 2b is a cross section through the injection needle according to FIG. 2a, FIG. 2c is a cross section through the injection needle according to the second embodiment, in a flexible, second state.
Figure 2C:
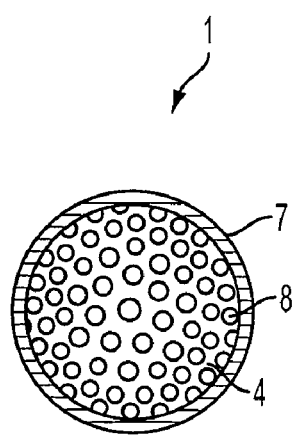

A second embodiment of an injection needle 1 according to the invention is shown in FIGS. 2a through 2c. As is shown in FIG. 2a, the injection needle 1 has an elastic tube 7 made from a shape-memory material. The tube 7 encloses a filler material 8 in the form of a fiber bundle which extends along the longitudinal axis of the injection needle 1. In a first state, the shape-memory material encloses the fiber bundle 8 firmly so that the fibers of the bundle 8 are accommodated in a tightly packed formation in the tube 7. The individual fibers of the bundle 8 lie tightly against one another so that they support one another and no hollow space is left in the inside of the tube 7. In the first state, therefore, bending of the injection needle 1 is counteracted by the frictional forces between the fibers. In this state, the injection needle 1 can be pushed into body tissue. At a front end, the tube 7 has two beveled edges, so that a tip 3 for insertion of the injection needle into the tissue is formed. FIG. 2b shows a cross section of the injection needle in the rigid, first state, i.e. resistant to bending, in which state the fibers of the bundle 8 lie tightly against one another inside the tube 7.

After introduction into the body tissue, the tube 7 is stimulated to change to a second state in which the individual fibers of the bundle 8 are no longer pressed against one another, or at any rate are only loosely pressed against one another, so that the clearance space between them serving as the channel 4 is either increased in size or is obtained for the first time. In this form, the fibers of the loosened bundle 8 can move and bend relative to one another.

The filler material 8 of the tube 7 does not have to be in the form of fibers, although such a filler material is preferred. Other suitable forms are also possible in principle, as long as the injection needle 1, in a first state, has sufficient rigidity for insertion into tissue, and, in a second state, has sufficient flexibility. For example, the filler material 8 could also be in the form of small spheres. The tube 7 would enclose and press together such a filler material.

Figure 3A:
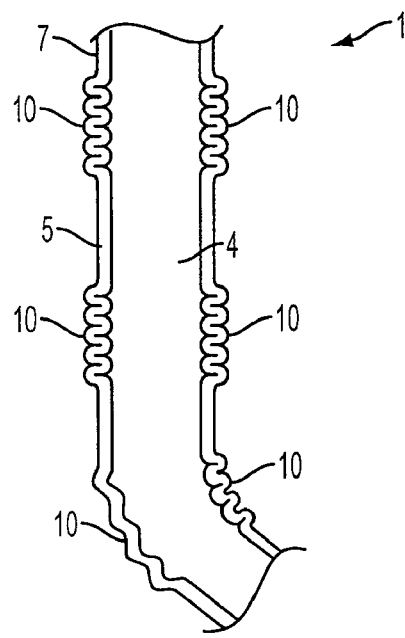
FIG. 3a is a schematic longitudinal section through another embodiment of an injection needle according to the present invention.

A third embodiment of an injection needle 1 according to the invention is shown in FIG. 3a. The injection needle 1 is of a tubular configuration. It is advantageously made from a shape-memory material. Formed in the wall 5 of a tube 7, at regular intervals along the longitudinal axis of the injection needle, there are fold areas 10 at which the wall 5 has circumferentially extending folds arranged next to one another in the longitudinal direction of the longitudinal axis of the injection needle. It is also conceivable to produce only the fold areas 10 from shape-memory material and to use another material for the tube sections lying between these.

In a first state, the individual fold layers of the fold areas 10 bear on one another. Further pressing-together of the fold areas 10 in the longitudinal direction of the longitudinal axis of the injection needle is not possible. When a force acts on the injection needle 1 in the longitudinal direction of the longitudinal axis of the injection needle, the injection needle 1 is therefore rigid. When a force is applied acting in a radial direction with respect to the longitudinal axis of the injection needle, the injection needle 1 can be bent at the fold areas 10 relative to the longitudinal axis. In this way, the individual folds of the fold areas 10 open out, as is shown at the lowermost fold area 10 in FIG. 3a. If the fold areas are made from shape-memory material, the rigidity, upon application of a force in the longitudinal direction, can be supported by a first form of the shape-memory material in which the folding of the fold areas 10 cannot be drawn apart. In a second form, when the injection needle 1 is inserted into body tissue, the shape-memory material at the fold areas 10 can be folded apart so that the injection needle is flexible in the inserted state.

Figure 3B:
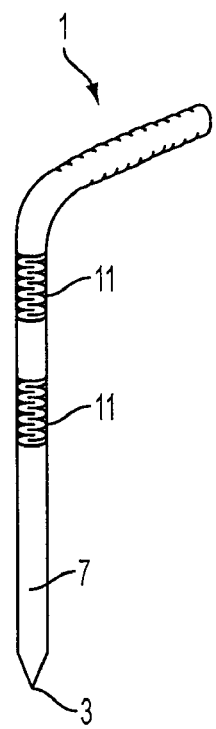
FIG. 3b is a schematic representation of a fourth embodiment of an injection needle according to the invention.

FIG. 3b shows a fourth embodiment of the injection needle 1 according to the invention which is similar to the third embodiment from FIG. 3a. Instead of the fold areas 10, perforation areas 11 are provided in the fourth embodiment. In the perforation areas 11, a wall of a tube 7 has small slits arranged one after the other in the circumferential direction. Individual rows of slits are arranged next to one another in the longitudinal direction of the longitudinal axis of the injection needle, the slits being mutually offset. If the slits are provided right through the wall, a thin elastic skin, for example, can be provided inside the tube so that no fluid escapes from the injection needle through the slits. However, such a skin can also be omitted if, for example, the fluid is to be delivered across a large surface area inside the tissue and not at one exact point. The slits, however, can also be configured in such a way that they reach far into an internal or external surface of the tube but do not extend through the wall of the tube.

When a force acts on the injection needle 1 in the longitudinal direction, the slits lie close together so that the injection needle is sufficiently rigid to be inserted into body tissue. When a force is applied acting in a radial direction with respect to the axis of the injection needle, the slits in the perforation areas 11 open on one side so that the injection needle is flexible at the opposite side relative to the longitudinal axis of the injection needle. The perforation of the perforation areas 11 can assume a great many different forms, for example it can also be undulating.

Figure 3C:
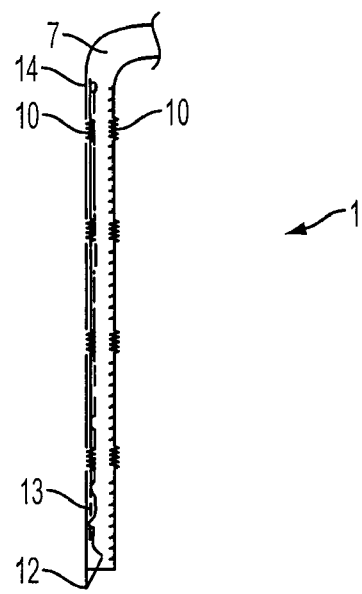
FIG. 3c is a schematic representation of the embodiment of FIG. 3a, FIG. 4a is a schematic representation of a fifth embodiment of an injection needle according to the present invention, in a rigid, first state.

FIG. 3c shows an injection needle 1 according to the third embodiment as shown in FIG. 3a, this injection needle 1 additionally having an insertion aid 12. As has been described above, the tube 7 of the injection needle has fold areas 10 in some places. The insertion aid 12 comprises an insertion tip 12 arranged on an extension 13. The extension 13 is arranged in the inside of the tube 7 in such a way that the insertion tip 12 protrudes from the end of the tube 7 in a first state of the injection needle. The extension 13 is secured at an attachment point 14 in the inside of the tube 7. The attachment point 14 lies at a site inside the tube 7 such that several fold areas 10 are located between the attachment point 14 and the end of the tube 7. In a second state, the folds of the fold areas 10 of the tube 7 are unfolded, that is to say drawn apart, so that the distance from the attachment point 14 to the end of the tube increases. In the second state, the tube slides over the insertion tip 12 of the insertion aid. In this state, it forms a protection against injuries on the insertion tip 12.

Figure 4A:
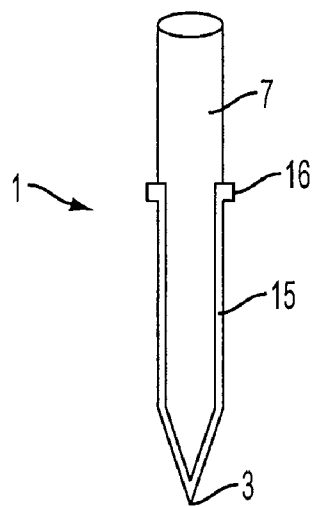
FIG. 4b is a schematic representation of the injection needle according to the fifth embodiment, in a flexible, second state.
Figure 4B:
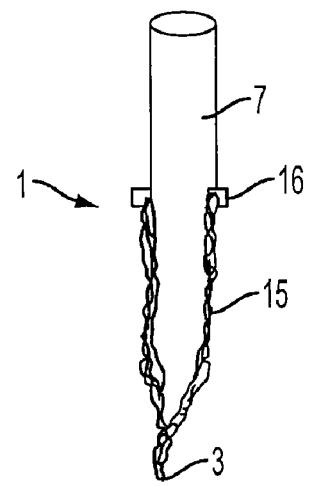

FIGS. 4a and 4b show a fifth embodiment of an injection needle 1 according to the invention. The injection needle has a tube 7 which, at one end intended for insertion into body tissue, has a hollow space 15 in its wall, said hollow space 15 extending, in the circumferential direction, about the entire circumference of the wall and extending, in the longitudinal direction, more or less along the entire length of the injection needle by which the injection needle is to be inserted into a tissue. The hollow space 15 is filled with a gel. In a first state, the gel has a solid form so that the injection needle 1 is sufficiently rigid to be inserted into body tissue. By stimulation of the gel, for example the temperature or a change in pH, the gel assumes a soft state so that the injection needle 1 is flexible. At the end of the hollow space 15 or of the tube 7, the hollow space or tube is designed tapering to a point in order to form a tip 3 for insertion into the tissue. At the end remote from the tip 3, a switching element 16 can be arranged on the hollow space 15 and provides, for example, stimulation of the gel in order to trigger a change of state. The switching element 16 can form a switch which, at the time of injection, can be triggered in particular by mechanical pressure or otherwise and whose triggering brings about the change of state of the gel.

Figure 5:
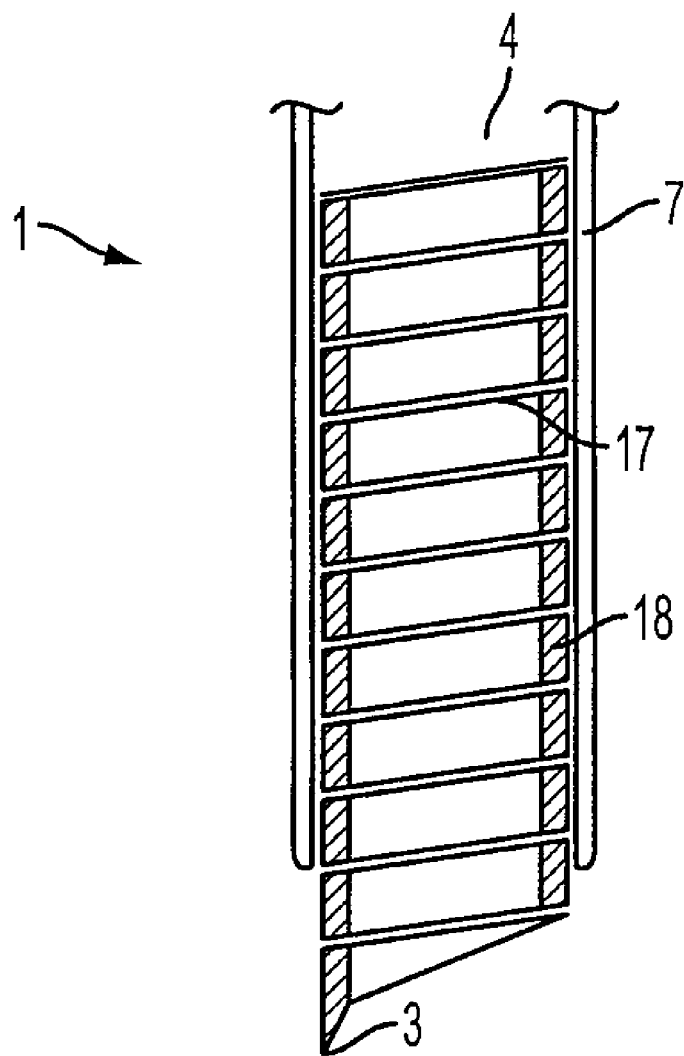
FIG. 5 is a longitudinal section through a sixth embodiment of an injection needle according to the invention.

FIG. 5 shows a sixth embodiment of an injection needle 1 according to the invention. The injection needle 1 comprises a tube 7 whose inner channel 4 receives a support structure 17 in the form of a helical spring 17. Spacers 18 extend substantially radially between the individual windings of the helical spring 17. The individual windings bear on the edges of the spacers 18. When a force acts on the injection needle in the longitudinal direction, the individual spacers 18 are pressed onto one another in this direction. The spacers 18 are of a non-elastic configuration, so that the injection needle is rigid when the force is applied in the longitudinal direction, and it can be inserted into a tissue. When a force is applied acting in a radial direction with respect to the longitudinal axis of the injection needle, from one side of the injection needle, the windings of the helical spring 17 on the opposite side move away from one another. The distance between the windings on this side becomes greater than the length of the spacers 18. On the other side, the windings remain bearing on the spacers 18. When a force is applied from the side onto the injection needle, the injection needle, as a result of the spreading apart of the windings of the helical spring 17, is able to yield to this force.

Figure 6A:
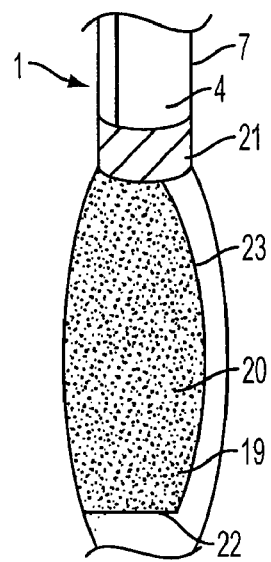
FIG. 6a is a longitudinal section through a seventh embodiment of an injection needle according to the invention, in a rigid, first state.
Figure 6B:
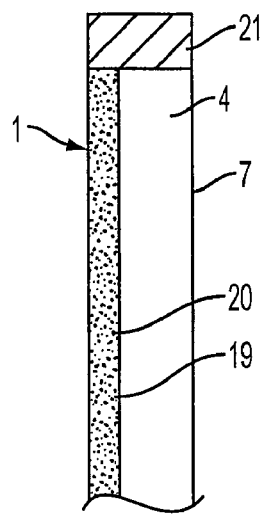
FIG. 6b is a longitudinal section through a seventh embodiment of an injection needle according to the invention in a flexible, second state.

FIGS. 6a and 6b show a seventh embodiment of an injection needle 1 according to the invention. The injection needle 1 comprises a tube 7 which, in its wall, has a clearance space 19 extending in the longitudinal direction of the longitudinal axis of the injection needle and separated from the channel 4 by a partition wall 23. The clearance space 19 preferably does not extend completely in the circumferential direction about the circumference of the tube 7. A filler material 20, for example granules, is provided in the clearance space 19.

In FIG. 6a, the injection needle 1 is shown in a first state in which a ring 21, arranged around the tube 7 of the injection needle 1, compresses the granules 20 in the clearance space 19. To do this, the ring 21 is moved along the tube 7 in such a way that the filler material 20 is pressed in the direction of an end wall 22 of the clearance space 19. The partition wall 23 between the clearance space 19 and the channel 4 for passage of a fluid is preferably more elastic than the material of the tube 7. By compression of the filler material as the ring 21 moves along the tube 7, the partition wall 23 is therefore expanded in the direction of the channel and of the opposite inside wall of the tube until it comes to bear on the opposite inside wall of the tube. In the compressed state of the filler material, the latter assumes a tightly pressed and rigid form, so that it has a stiffening effect on the tube 7 of the injection needle 1. The injection needle can be inserted into body tissue in this state.

In FIG. 6b, the ring 21 has been moved back along the tube 7, that is to say farther away from the end wall 22. In this state, the filler material 20 spreads along a greater length inside the clearance space 19, so that the partition wall 23 moves back and frees the channel 4 for passage of a fluid. This results in a short distance between the inside wall of the tube and the partition wall between which the filler material 20 is arranged, so that there is only a thin material layer. In this second state, in which the ring 21 has freed the filler material from its compression, the filler material 20 is movable in the clearance space 19 and the injection needle is flexible. In principle, it is also possible, instead of a single clearance space, to provide several clearance spaces arranged along the longitudinal axis of the injection needle or tube 7. Moreover, the filler material can, for example, comprise a shape-memory material, in the same way as has been described in the second embodiment.

FIGS. 7a and 7b show an injection needle 1 in an eighth embodiment. The injection needle 1 is made from a homogeneous shape-memory material along its entire length to be inserted into the tissue. In the first state, shown in FIG. 7a, it is straight and has a sufficient flexural strength for insertion into the tissue. It can be made, in particular, from a thermoplastic polymer. FIG. 7b shows the injection needle 1 of the eighth embodiment after insertion into the tissue. Because of the conditions prevailing in the tissue, the material of the injection needle 1 has changed from the first state to the second state in which it is so pliable that it bends elastically under the loads occurring in the tissue. The elastic modulus of the material of the eighth embodiment reduces under the conditions prevailing in the tissue. In ambient conditions outside the tissue, it has an elastic modulus of preferably at least about 3000 MPa. In the inserted state, by contrast, it only has an elastic modulus of at most about 1000 MPa, for example 700 MPa. The change of state can in particular be brought about by transition of the polymer to the amorphous state. The change of state is preferably effected by a change in temperature, since the polymer has a glass transition temperature which lies at or is preferably slightly below the tissue temperature but is above the normal ambient temperatures. The glass transition temperature should therefore be at least about 30° C., preferably at least about 32° C., and should at most correspond to body temperature, preferably at most about 36° C. The injection needle 1 is provided with a tip which forms a sharp cutting edge. This tip is advantageously also so soft, in the inserted state, that it is no longer able to cut. The injection needle 1 of the eighth embodiment in the first state and in the second state is an injection cannula, i.e. in both states it has an inner channel 4 for the passage of the fluid that is to be administered.

FIGS. 8a and 8b show an injection needle 1 in a ninth embodiment, which is likewise a cannula in both states. In the ninth embodiment, the injection needle 1 is made along its entire length from a composite material as tube 7. The composite material is composed of a support matrix made from a first material 24 and of solid particles 25 embedded in the support matrix. The volume proportion of the solid particles 25 decreases continuously from the tip of the injection needle 1 toward its proximal end. Directly at the cutting edge formed at the tip, the volume proportion of the filler material 25 is about 70% and it decreases toward the proximal end of the injection needle 1, i.e. along the length of the injection needle 1 to be inserted into the tissue, to a proportion below about 20%, preferably to about 10 to 15%. The material of the support matrix 24 is again a material whose elastic modulus in the inserted state is less than before insertion. In particular, a thermoplastic polymer can form the support matrix material, and the statements concerning the eighth embodiment preferably apply to the polymer. The tube 7 is rigid at ambient conditions outside the body and, in this first state, can be regarded as forming a pipe for insertion. In the second state, it is elastically flexible.

While exemplary embodiments, including preferred embodiments, of the present invention, its making and its use have been described herein, it is contemplated that various modifications could be made without deviating from the spirit of the present invention. Accordingly, it is intended that the scope of the present invention be dictated by the appended claims.

The invention claimed is:

1. An injection needle for injection into body tissue,
    said injection needle having a pre-insertion state and an inserted state, being rigid in the pre-insertion state and flexible in the inserted state, having a channel for introduction of a fluid in the inserted state, the transition from rigid to flexible occurring after insertion into the body tissue, wherein
    the injection needle is made at least partly from at least one material which, in the pre-insertion state, has a flexural strength sufficient for the injection and, in the inserted state, has a reduced flexural strength, and
    the injection needle is rigid when a force acts on the injection needle in the longitudinal direction and is flexible when a force acts in the radial direction relative to the longitudinal axis of the injection needle; and
    wherein that the injection needle further comprises, in the pre-insertion state, at least one edge extending in the longitudinal direction on its circumference and, in the inserted state, an edgeless circumference.

2. The injection needle as claimed in claim 1, wherein the injection needle is made at least partly from a shape-memory material.

3. The injection needle as claimed in claim 1, wherein the injection needle is made from a shape-memory material along its entire length.

4. The injection needle as claimed in claim 1, wherein the material changing state has an elastic modulus of over 1000 MPa in the pre-insertion state and an elastic modulus of below 1000 MPa in the inserted state.

5. The injection needle as claimed in claim 1, wherein the material changing its state has an elastic modulus of at least 3000 MPa in the pre-insertion state and an elastic modulus of at most 800 MPa in the inserted state.

6. The injection needle as claimed in claim 1, wherein a change of state from the pre-insertion state to the inserted state is obtained through a means of changing state which applies at least one of a voltage and radiation to the injection needle.

7. The injection needle as claimed in claim 1, wherein the change of state is reversible.

8. An injection needle for injection into body tissue,
    said injection needle having a pre-insertion state and a inserted state, being rigid in the pre-insertion state and flexible in the inserted state, having a channel for introduction of a fluid in the inserted state, the transition from rigid to flexible occurring after insertion into the body tissue, wherein
    the injection needle is made at least partly from at least one material which, in the pre-insertion state, has a flexural strength sufficient for the injection and, in the inserted state, has a reduced flexural strength, and
    the injection needle is rigid when a force acts on the injection needle in the longitudinal direction and is flexible when a force acts in the radial direction relative to the longitudinal axis of the injection needle; and
    wherein the injection needle, in the pre-insertion state, is designed without an inner hollow space and, in the inserted state, is designed with an inner channel along the longitudinal axis of the injection needle.

9. The injection needle as claimed in claim 8, wherein the injection needle is made at least partly from a shape-memory material.

10. The injection needle as claimed in claim 8, wherein the injection needle is made from a shape-memory material along its entire length.

11. The injection needle as claimed in claim 8, wherein the material changing state has an elastic modulus of over 1000 MPa in the first state and an elastic modulus of below 1000 MPa in the second state.

12. The injection needle as claimed in claim 8, wherein the material changing its state has an elastic modulus of at least 3000 MPa in the pre-insertion state and an elastic modulus of at most 800 MPa in the inserted state.

13. The injection needle as claimed in claim 8, wherein a change of state from the first state to the second state is obtained through a means of changing state which applies at least one of a voltage and radiation to the injection needle.

14. The injection needle as claimed in claim 8, wherein the change of state is reversible.

15. An injection needle for injection into body tissue,
said injection needle having a pre-insertion state and a inserted state, being rigid in the pre-insertion state and flexible in the inserted state, having a channel for introduction of a fluid in the inserted state, the transition from rigid to flexible occurring after insertion into the body tissue, wherein
the injection needle is made at least partly from at least one material which, in the pre-insertion state, has a flexural strength sufficient for the injection and, in the inserted state, has a reduced flexural strength, and
the injection needle is rigid when a force acts on the injection needle in the longitudinal direction and is flexible when a force acts in the radial direction relative to the longitudinal axis of the injection needle; and
wherein the injection needle, in the pre-insertion state, has a closed tip, and, in the inserted state, has an opening adjacent to the tip.

16. The injection needle as claimed in claim 15, wherein the injection needle is made at least partly from a shape-memory material.

17. The injection needle as claimed in claim 15, wherein the injection needle is made from a shape-memory material along its entire length.

18. The injection needle as claimed in claim 15, wherein the material changing state has an elastic modulus of over 1000 MPa in the pre-insertion state and an elastic modulus of below 1000 MPa in the inserted state.

19. The injection needle as claimed in claim 15, wherein the material changing its state has an elastic modulus of at least 3000 MPa in the pre-insertion state and an elastic modulus of at most 800 MPa in the inserted state.

20. The injection needle as claimed in claim 15, wherein a change of state from the pre-insertion state to the inserted state is obtained through a means of changing state which applies at least one of a voltage and radiation to the injection needle.

21. The injection needle as claimed in claim 15, wherein the change of state is reversible.

* * * * *